United States Patent [19]

Cortese, Jr. et al.

[11] Patent Number: 4,521,629

[45] Date of Patent: Jun. 4, 1985

[54] METHOD FOR THE PREPARATION OF 1,5-BIS-ARYL-1,4-PENTADIEN-3-ONES

[75] Inventors: Nicholas A. Cortese, Jr., Trenton, N.J.; William H. Gastrock, Vicksburg, Miss.

[73] Assignee: American Cyanamid Company, Stamford, Conn.

[21] Appl. No.: 626,168

[22] Filed: Jun. 29, 1984

[51] Int. Cl.$^3$ ............................................. C07C 45/61
[52] U.S. Cl. .................................. 568/313; 568/306; 260/465 F; 260/465 F; 260/465 G; 564/441; 564/442; 564/443; 564/305
[58] Field of Search ............... 568/313, 306, 390, 345; 260/465 DF, 465 F, 465 G; 564/441, 442, 443, 305

[56] References Cited

U.S. PATENT DOCUMENTS

| | | | |
|---|---|---|---|
| 3,194,841 | 7/1965 | Alphen et al. | 568/313 |
| 3,389,986 | 6/1968 | Di Bella | 568/313 |
| 4,005,147 | 1/1977 | Fischer et al. | 568/345 |
| 4,035,395 | 7/1977 | Stitter et al. | 568/313 |
| 4,182,729 | 1/1980 | Collins | 568/313 |
| 4,215,076 | 7/1980 | Stueben | 568/461 |

OTHER PUBLICATIONS

Wattanasin et al., Synthesis, 1980, pp. 647–650.
Dickinson, J. Chem. Soc., 1927, pp. 1888–1892.
Esikova et al., Chem. Abst., vol. 93, #94441q(1980).
Yufit et al., Chem. Abst., vol. 93, #131679w(1980).

*Primary Examiner*—James H. Reamer
*Attorney, Agent, or Firm*—H. G. Jackson

[57] ABSTRACT

The invention relates to a method for the preparation of certain substituted bis-arylpentadienones which are useful and valuable intermediates for the preparation of insecticidal amidinohydrazones. The invention further relates to pentadienone substituted amidimohydrazone insecticides and fire ant control agents.

9 Claims, No Drawings

METHOD FOR THE PREPARATION OF 1,5-BIS-ARYL-1,4-PENTADIEN-3-ONES

SUMMARY OF THE INVENTION

The invention is a method for the preparation of compounds of formula (I):

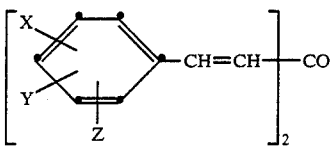

wherein X, Y, and Z each are independently selected from the group consisting of hydrogen, $C_1$-$C_3$ alkyl, $C_1$-$C_3$ haloalkyl, $C_1$-$C_3$ alkoxy, $C_1$-$C_3$ haloalkoxy, halogen, $NO_2$, CN, $R_1R_2N$—, and $R_1R_2NO_2S$—; $R_1$ and $R_2$ each are selected from hydrogen or $C_1$-$C_3$ alkyl.

The compounds of formula (I) are useful and valuable intermediates for the preparation of certain insecticidal amidinohydrazones of formula (II).

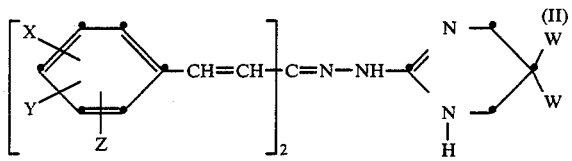

wherein X, Y, and Z are as hereinabove defined, and W is hydrogen or methyl. The insecticides of formula (II) are especially valuable for the control of fire ants, and cockroaches, and are disclosed in U.S. Pat. Nos. 4,163,102 and 4,191,768, incorporated herein by way of reference. Pentadienone substituted amidinohydrazones are also disclosed in U.S. Pat. No. 3,878,201 (1975), as antimalarial and antitubercular agents for warm-blooded animals.

A preferred group of compounds represented by formula (I) are those wherein Y and Z are both hydrogen; X is methyl, trifluoromethyl, methoxy, di- and trifluoromethoxy, Br, Cl, F, $NO_2$, CN, and $(CH_3)_2N$.

A more preferred group of compounds of formula (I) are those wherein Y and Z are both hydrogen; X is located in the para position and is selected from methyl, trifluoromethyl, methoxy, di- and trifluoromethoxy, Br, Cl, F, $NO_2$, CN, and $(CH_3)_2N$.

The most preferred compound of formula (I) is graphically illustrated as follows:

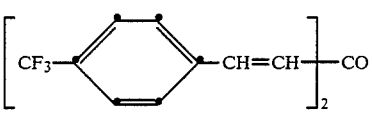

Pentadienones of formula (I) usually are prepared by a base catalyzed condensation reaction, as follows: two moles of an aldehyde of formula (III)

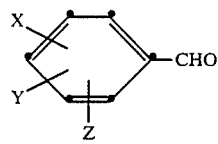

wherein X, Y, and Z are as hereinabove defined, are reacted with one mole of acetone in the presence of water and an inert solvent selected from lower alcohols, $C_5$-$C_8$ aliphatic hydrocarbons, petroleum distillates, benzene, toluene, xylene and the like, and mixtures thereof, and in the presence of a dilute aqueous solution of a base selected from alkali metal hydroxides, carbonates, and bicarbonates, preferably sodium hydroxide. The base is usually added last, in small portions to the reaction mixture, after all of the other components have been combined, and over a period of time from about one hour to about three hours, and at a temperature range of from about 20° C. to about 50° C. until the reaction is essentially complete. The pH of the reaction mixture is then lowered to below 7 with an inorganic acid such as hydrochloric sulfuric-, or phosphoric acid, the mixture is then heated at the reflux for a period of time of from about one hour to about three hours, is cooled down, and the product isolated by standard laboratory procedures. The thus obtained pentadienone is usually sufficiently pure to be used directly in the preparation of formula (II) insecticides, however it may be further purified, if so desired. The above reaction scheme may be graphically illustrated as follows:

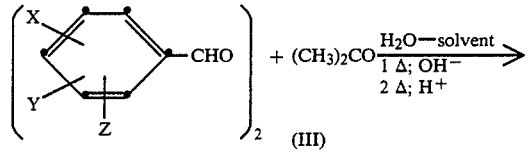

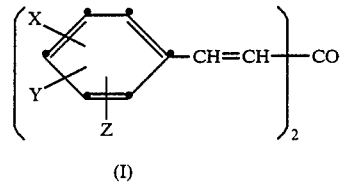

wherein X, Y, and Z are as hereinabove defined.

We now find, that by the method and procedure of the invention the compounds of formula (I) may be prepared in significantly increased yields and improved purity.

Thus, two molar equivalents of an aldehyde of formula (III)

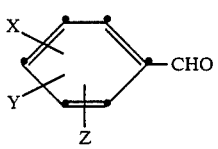

wherein X, Y, and Z each are selected from the group consisting of hydrogen, $C_1$-$C_3$ alkyl, $C_1$-$C_3$ haloalkyl, $C_1$-$C_3$ alkoxy, $C_1$-$C_3$ haloalkoxy, halogen, $NO_2$, CN, $R_1R_2N$—, and $R_1R_2NO_2S$—; $R_1$ and $R_2$ each are selected from hydrogen or $C_1$-$C_3$ alkyl; are dissolved in a solvent selected from the group consisting of $C_5$-$C_8$ aliphatic hydrocarbons, petroleum distillates, benzene, toluene, xylene, and the like, preferably hexane or heptane. The solution is then blanketed with an inert gas, such as nitrogen. Next, water and an aqueous solution of a base selected from alkali metal hydroxides, carbonates, and bicarbonates, preferably sodium hydroxide is added in amounts of from about 3 mol percent to about 25 mol percent, and preferably in amounts of from 5 to 15 mol percent based on the aldehyde. The amount of water and the concentration of the aqueous base are chosen in such a manner that the ultimate concentration of the base in the aqueous phase of the reaction mixture is approximately 3% w/v. The reaction mixture is stirred at a temperature range of from about 20° C. to about 55° C., preferably from about 35° C. to about 45° C., and a mixture of approximately 1.0 to 1.1 moles of acetone, and a phase transfer agent used in amounts of from about 1% by weight to about 10% by weight, and preferably 2 to 5% by weight on the weight of said formula (III) aldehyde, and selected from the compounds represented by formula (IVa) or (IVb)

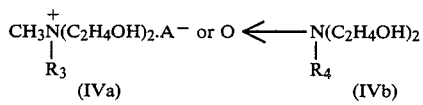

(IVa)                              (IVb)

wherein $R_3$ is selected from —$(CH_2)_{11}CH_3$, —$(CH_2)_8CH=CH-(CH_2)_7CH_3$, and —$(CH_2)_{17}CH_3$; $R_4$ is tallowyl or —$(CH_2)_{11}CH_3$; A is Cl, Br or I optionally dissolved in hexane or heptane, is added over a period of time of from about three hours. On completion of the addition the reaction mixture is stirred at a temperature range of from about 20° C. to about 55° C., and preferably from about 35° C. to about 45° C., for a period of time of from about one to about three hours. Next, the reaction mixture is diluted with a $C_1$-$C_4$ alcohol, preferably isopropyl alcohol and a mineral acid, selected from hydrochloric-, sulfuric-, or phosphoric acid is added in amounts sufficient to lower the pH of the reaction mixture to a range of from about pH 5 to about pH 1, and preferably to about pH 1 to 2. The reaction mixture is then heated at reflux for a period of time from about one to about three hours, cooled down and the desired product of formula (I) isolated by standard laboratory procedures, and further purified if so desired. The above described novel procedure affords the compounds of formula (I) in over 80% yields, and in purities approaching 100%.

It should be noted that in the above procedure equally good results may be obtained by incorporating the phase transfer agent into the starting mixture, and adding the acetone last (neat or if so desired dissolved in the appropriate solvent).

As stated above, the compounds of formula (I) are useful and valuable intermediates for the preparation of certain insecticidal amidinohydrazones, such as represented and defined by formula (II) above.

Conveniently, a one molar equivalent of an appropriately substituted hydrazine salt of formula (IV)

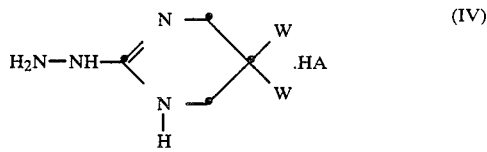

where W is as hereinabove defined and HA represents a mineral acid such as hydrochloric-, hydrobromic-, or hydriodic acid, is reacted with at least one molar equivalent of a pentadienone of formula (I) as defined above in the presence of an anhydrous $C_1$-$C_3$ alcohol and a small amount of the acid selected from those listed above, for a period of time of from about one hour to about three hours or until the reaction is essentially complete, and then the thus obtained compound of formula (II) is isolated by standard laboratory procedures, and further purified, if so desired. The above reaction scheme may be illustrated as follows:

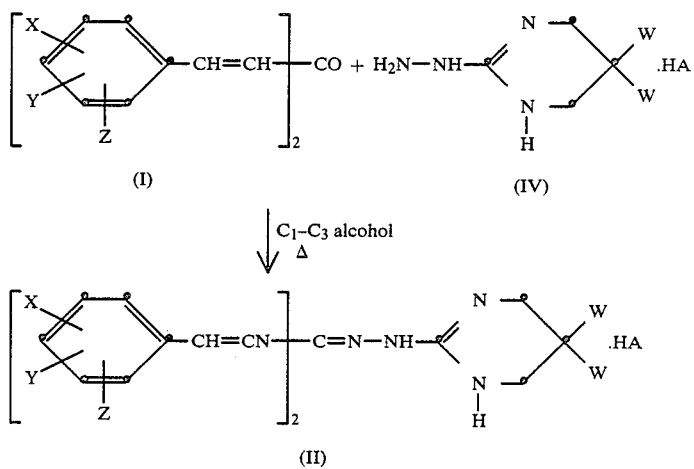

wherein X, Y, Z, W, and HA are defined as above.

In general, the compounds of formula II are especially active and quite selective against Lepidopterous larvae such as southern armyworms [*Spodoptera eridania* (Cramer)], cabbage loopers [*Trichoplusia ni* (Hübner)], tobacco budworms [*Heliothis virescens* (Fabricius)], and the like, at 10 to 1,000 ppm rates. They do not appear to be especially toxic to most beneficial insects and thus are useful for pest management and integrated control programs.

The above compounds (II) are also active as stomach poisons. Thus, they are effective against insects with chewing mouth parts (Orthopterous insects such as cockroaches, grasshoppers, crickets and Isopterous insects, such as termites) as well as those with sponge and lapping mouth parts (Dipterous insects, such as flies). They are effective for the control of fire ants, such as the southern fire ant, *Solenopsis xyloni*, the black imported fire ant, *Solenopsis richteri* and the red imported fire ant, *Solenopsis invicta*. They are also effective for the control of ants, such as the big-headed ant, *Pheidole megacephala*, and the Argentine ant, *Iridomyrmax humilis*, and for the control of many species of ants that are classified under the general category of household ants.

The invention is further illustrated by the examples set forth below. These examples are provided only by way of illustration and are not intended to be limiting.

EXAMPLE 1

Preparation of 1,5-bis($\alpha,\alpha,\alpha$-trifluoro-p-tolyl)-1,4-pentadien-3-one by the process of the invention A mixture of 4-trifluoromethylbenzaldehyde (65.2 g; 0.369 mol), heptane (70 ml), 10% sodium hydroxide solution (15 g) and water (30 ml) is stirred under a nitrogen atmosphere and heated to 40° C. Next, a solution of acetone (10.7 g) and of bis(2-hydroxyethyl)methyloleylammonium chloride (1.6 g) in heptane (30 ml) is added dropwise over three hours at the above temperature. After the addition is completed, the mixture is stirred at 40° C. to 45° C. for two hours. After two hours, isopropyl alcohol (68 ml) and hydrochloric acid (9.4 ml; concentrated) are added and the mixture heated at reflux for 1.5 hours. The reaction mixture is then cooled to 20° C., the precipitated solid is isolated by filtration, washed with heptane (40 ml) and water to afford 56.8 g of 99.6% pure title product, mp 154° C. to 156° C. (83.0% yield).

EXAMPLE 2

Preparation of 1,5-bis-($\alpha,\alpha,\alpha$-trifluoro-p-tolyl)-1,4-pentadien-3-one The preparation of Example 1 is repeated, excepting that the bis(2-hydroxyethyl)methyloleylammonium chloride phase transfer agent (1.6 g) is added to the aldehyde-heptane-water-sodium hydroxide mixture. This mixture is heated to 40° C. under a nitrogen atmosphere, and the solution of acetone in heptane added under the conditions and by the method of Example 1. The reaction affords 55.1 g of title product, 99.4% pure, mp 153° C. to 156° C. (yield: 80.3%).

The above experiment is repeated, except that less water (15 g) is used, and the amount of phase transfer agent is doubled. The title product is obtained in 99.0% purity, mp 154° C. to 156° C. (yield: 77.9%).

EXAMPLE 3

Preparation of 1,5-bis($\alpha,\alpha,\alpha$-trifluoro-p-tolyl)-1,4-pentadien-4-one using a phase transfer agent A solution of 4-trifluoromethylbenzaldehyde (64.0 g; 0.369 mol) in heptane (70 ml) is stirred under a nitrogen atmosphere, then 10% aqueous sodium hydroxide (15 g), water (15 g), and dodecylbis(2-hydroxyethyl)methylammonium bromide are added. Next, a solution of acetone (10.7 g; 0.184 ml) in heptane (30 ml) is added at 25° C. to 30° C. over a period of time of four hours. The mixture is stirred for an additional two hours at 25° C. to 30° C. then concentrated hydrochloric acid (9.4 ml), and isopropyl alcohol (48 ml) are added, and the reaction mixture heated at reflux for 1.5 hours. It is then cooled to 20° C., the precipitated solid filtered, washed with heptane (40 ml) and water, and dried to yield 53.7 g of title product, 99.6% pure, mp 153° C. to 155° C. (yield: 78.6%).

The above preparation is repeated several times, on the same scale and under essentially identical conditions. The data obtained are recorded in Table I below.

TABLE I

Preparation of 1,5-bis($\alpha, \alpha, \alpha$-trifluoro-p-tolyl)-1,4-pentadien-3-one by the method of Example 3; summary data

| No. | % Purity of Sample | % Yield | mp in °C. | Remarks |
|---|---|---|---|---|
| 1 | 98.1 | 76.9 | 153–155 | |
| 2 | 99.3 | 83.4 | 153–155 | |
| 3 | 97.1 | 81.9 | 153–155 | |
| 4 | 97.2 | 74.9 | 153–155 | Only 1/5 of phase transfer agent used. |
| 5 | 99.6 | 79.6 | 154–156 | |
| 6 | 99.9 | 78.8 | 154–156 | |
| 7 | 99.4 | 84.2 | 153–155 | |
| 8 | 98.5 | 78.8 | 154–156 | |
| 9 | 98.7 | 78.3 | 154–156 | |
| 10 | 98.9 | 79.0 | 154–156 | Only ½ of phase transfer agent used. |
| 11 | 98.8 | 79.1 | 154–156 | Approximately ½ of phase transfer agent Cl⁻ salt used. |

The average of the above yields is 79.54%.

Similar preparations, using octadecylbis(2-hydroxyethyl)methylammonium chloride (1.6 g) and
a. phosphoric acid (6.1 ml; 85%);
b. concentrated sulfuric acid (4.8 ml);
c. hydrochloric acid, to adjust pH to 5.5;
afford the product:
a. purity: 99.3%; yield: 80.9%; mp 154° C.–156° C.;
b. purity: 99.8%; yield: 81.5% mp 154° C.–156° C.;
c. purity: 99.6%; yield: 80.3%; mp 154° C.–156° C.;

EXAMPLE 4

Preparation of 1,5-bis($\alpha,\alpha,\alpha$-trifluoro-p-tolyl)-1,4-pentadien-3-one using a phase transfer agent A solution of 4-trifluoromethylbenzaldehyde (64.2 g; 0.369 mol) in heptane (70 ml) is stirred under a nitrogen atmosphere, then sodium hydroxide (15 g; 10% aq), water (30 g), and bis(2-hydroxyethyl)tallowamine N-oxide (6 g) are added. Next a solution of acetone (10.7 g; 0.184 mol) in heptane (30 ml) is added at 25° C. to 35° C. over a period of two hours. The resulting slurry is then stirred for two hours at 25° C. to 30° C. Concentrated hydrochloric acid (9.4 ml) and isopropyl alcohol (48 ml) are then added and the mixture heated at reflux for 1.5 hours, and is then cooled to 20° C. The solid is filtered, washed with heptane (40 ml) and water, and is dried to afford 54.5 g of 99.9% pure title product (yield: 79.1%), mp 153° C. to 155° C.

Substituting bis(2-hydroxyethyl)cocoamine N-oxide for bis(2-hydroxyethyl)tallowamine N-oxide in the above reaction affords the product in 75.9% yield.

EXAMPLE 5

Preparation of 1,5-bis(α,α,α-trifluoro-p-tolyl)-1,4-pentadien-3-one

A solution of sodium hydroxide (15 g of 10% aqueous) is added with stirring, and under a nitrogen atmosphere to a solution of 4-trifluoromethylbenzaldehyde (6.42 g; 0.369 mol) in heptane (70 ml). Next, a solution of acetone (10.7 g; 0.184 mol) in heptane (30 ml) is added to the above two phase system at a temperature range of from 25° C. to 30° C. over a period of two hours. The reaction mixture is then stirred for two hours at 25° C. to 30° C. Concentrated hydrochloric acid (9.4 ml) and isopropyl alcohol (48 ml) are then added, the mixture heated at reflux for 1.5 hours, and is then cooled to 20° C. The precipitated solid is filtered, washed with heptane (40 ml), and water and dried under vacuum to afford 50.8 g of title product, 98.8% pure, mp 154° C. to 156° C. (yield: 73.7%).

a. The above preparation is repeated nineteen times on the same scale and under essentially similar conditions. The percent yields obtained are: 73.8; 68.0; 69.2; 70.0; 69.4; 67.5; 70.7; 72.5; 71.1; 71.8; 71.6; 75.0; 70.3; 74.4; 72.7; 72.1; 73.2; 71.5; 72.8. The average yield of these runs is 71.4%.

b. The above preparation is repeated seven times on the same scale and under similar conditions, excepting that the acetone is included in the reaction mixture at the start of the reaction, and that it is the sodium hydroxide solution which is added last to the reaction mixture over a period of time of one hour at room temperature. The percent yields obtained are: 65.5; 62.5; 68.9; 68.4; 63.4; 67.2; 68.2. The average yield of these runs is 66.3%.

EXAMPLE 6

Preparation of 1,5-bis(α,α,α-trifluoro-p-tolyl)-1,4-pentadien-3-one (1,4,5,6-tetrahydro-5,5-dimethyl-2-pyrimidinyl)hydrazone A mixture of 5,5-dimethyl-1,4,5,6-tetrahydroprimidin-2-yl hydriodide (2.1 g), 1,5-bis(α,α,α-trifluoro-p-tolyl)-1,4-pentadien-3-one (3.2 g), absolute ethanol (6 ml), and one drop of 47% hydriodic acid is heated at reflux for two to three hours and then cooled in ice. The precipitated yellow hydriodide salt is neutralized by stirring it with a mixture of ethyl acetate (15 ml) and saturated sodium carbonate solution (15 ml). The ethyl acetate layer is separated from the aqueous phase, dried over magnesium sulfate, and concentrated to give a red oil. The oil is mixed with a small amount of ether, and the mixture refrigerated. The resulting solid is filtered, washed with ether and dried to afford 1.2 g title compound, m; 163.5° C. to 164.5° C.

EXAMPLE 7

Preparation of 1,5-bis(α,α,α-trifluoro-p-tolyl)-1,4-pentadien-3-one on a large scale A mixture of 4-trifluoromethylbenzaldehyde (8.4 kg), heptane (12.1 L), water (5.23 L), 50% sodium hydroxide (0.384 kg) and methyl bis(hydroxyethyl)oleylammonium chloride (0.213 kg) is stirred under a nitrogen atmosphere and heated to 40° C. to 45° C. Acetone (1.44 kg) is added to the above mixture over 2.3 hours. The resulting slurry is stirred and heated at 42° C. for two hours and then 85% phosphoric acid (1.36 kg) is added followed by isopropyl alcohol (8.97 L). The resultant mixture is heated at reflux (73° C.) for 1.5 hours and then cooled to 14° C. The reaction mixture is filtered, the isolated solids washed with heptane (5.29 L) and water (7.12 L). Drying affords 7.2 kg of the title compound, mp 154° C. to 155.5° C.

EXAMPLE 8

Preparation of 1,5-bis(α,α, α-trifluoro-p-tolyl)-1,4-pentadien-3-one (1,4,5,6-tetrahydro-5,5-dimethyl-2-pyrimidinyl)hydrazone Concentrated hydrochloric acid (2 ml) is added to a mixture of 1,5-bis(α,α,α-trifluoro-p-tolyl)-1,4-pentadiene-3-one (51.1 g; 0.138 mol), 2-hydrazino-1,4,5,6-tetrahydro-5,5-dimethylpyrimidine hydrochloride (27.3 g; 0.145 mol), isopropyl alcohol (190 ml) and water (13.2 ml). The mixture is heated at 40° C. for one hour, the temperature is then increased to 55° C. to 60° C. and 50% sodium hydroxide (9.2 ml) added over a period of one to two hours at 60° C. Water (125 ml) is then added over one hour, the mixture cooled to 20° C. to 25° C. and filtered. The thus isolated product is washed with water and dried to afford 64.2 g of solid, mp 188° C. to 190° C.

We claim:

1. A method for the preparation of a compound of formula:

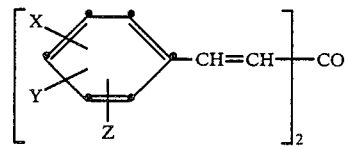

wherein X, Y, and Z each are independently haloalkyl, $C_1$-$C_3$ alkoxy, $C_1$-$C_3$ haloalkoxy, halogen, $NO_2$, CN, $R_1R_2N-$, or $R_1R_2NO_2S-$; $R_1$ and $R_2$ each are hydrogen or $C_1$-$C_3$: alkyl; comprising: admixing 2 molar equivalents of an aldehyde of formula:

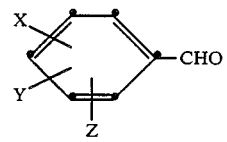

wherein X, Y, and Z are as herein above defined; with an inert solvent $C_5$-$C_8$ aliphatic hydrocarbons, petroleum distillates, benzene, toluene, or xylene; water, and with an amount of from 3 mol % to 25 mol % of the above aldehyde a base of an alkali metal hydroxide, carbonate, or bicarbonate as an aqueous solution; adding to the above mixture of from 1 to 1.1 molar equivalents of acetone, and from 1% by weight to 10% by weight on the weight of the above aldehyde, a phase transfer agent selected from formula:

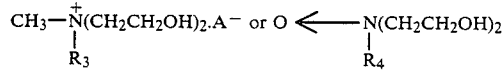

wherein $R_3$ is $-(CH_2)_{11}CH_3$, $-(CH_2)_8CH=CH-(CH_2)_7CH_3$, or $-(CH_2)_{17}CH_3$; $R_4$ is tallowyl or $-(CH_2)_{11}CH_3$; A is Cl, Br, or I; at a temperature range of from 20° C. to 55° C. over a period of time of from one to three hours; stirring the mixture at 20° C. to 55° C. for one to three hours; diluting the mixture with a $C_1$-$C_3$ alcohol, and adjusting the pH of the thus obtained mixture with a mineral acid in the range of from pH 5 to pH 1; and then heating the reaction mixture at reflux of from one to three hours, or until the reaction is essentially complete.

2. A method according to claim 1, wherein X is methyl, trifluoromethyl, methoxy, difluoromethoxy, trifluoromethoxy, Br, Cl, F, $NO_2$, CN, or $(CH_3)_2N$; and Y and Z both are hydrogen.

3. A method according to claim 1, wherein X is in the para position and is methyl, trifluoromethyl, methoxy, difluoromethoxy, trifluoromethoxy, Br, Cl, F, $NO_2$, CN, or $(CH_3)_2N$; and Y and Z both are hydrogen.

4. A method according to claim 1, wherein the compound is 1,5-bis($\alpha,\alpha,\alpha$-trifluoro-p-tolyl)-1,4-pentadien-3-one.

5. A method according to claim 1, wherein the inert solvent is hexane or heptane; the amount of base is 5 mol % to 15 mol %, and the base is sodium hydroxide or potassium hydroxide; the amount of phase transfer agent is of from 2% to 5% by weight; the temperature range of the addition is from 35° C. to 45° C.; the alcohol is isopropyl alcohol; the mineral acid is hydrochloric acid, and the pH range is from pH 1 to pH 2.

6. A method according to claim 1, wherein the phase transfer agent is bis(2-hydroxyethyl)-methyloleylammonium chloride, dodecyl bis(2-hydroxyethyl)methylammonium bromide, octadecyl bis(2-hydroxyethyl)-methylammonium chloride, bis(2-hydroxyethyl)-tallowamine N-oxide, or bis(2-hydroxyethyl)cocoamine N-oxide.

7. A method according to claim 1, wherein a mixture is prepared from two molar equivalents of p-trifluoromethylbenzaldehyde; heptane; water, 5 mol % to 15 mol % of sodium hydroxide; adding to the mixture 1 to 1.1 molar equivalent of acetone and 2% to 5% by weight of bis(2-hydroxyethyl)methyloleylammonium chloride at a temperature range of from 31° C. to 45° C. over a period of time of from one to three hours; stirring the mixture of 35° C. to 45° C. for one to three hours; diluting the mixture with isopropyl alcohol; adjusting the pH with hydrochloric acid to pH 1 to pH 2; and refluxing the mixture for a period of time sufficient to essentially complete the reaction.

8. A method according to claim 7, wherein a solution of 1 to 1.1 molar equivalent of acetone and 2% to 5% by weight of bis(2-hydroxyethyl)-methyoleylammonium chloride in heptane is added to the mixture.

9. A method according to claim 7, wherein 2% to 5% by weight of bis(2-hydroxyethyl)-methyloleylammonium chloride is added to the mixture of aldehydeheptane-water-sodium hydroxide.

* * * * *